US006238360B1

(12) United States Patent
Gildersleeve et al.

(10) Patent No.: US 6,238,360 B1
(45) Date of Patent: May 29, 2001

(54) DEVICE FOR CONFIGURING A JOINT BRACE

(75) Inventors: Richard E. Gildersleeve, Escondido; Theodore V. Tillinghast, Cardiff; John L. Danssaert, Jr., Solana Beach; James M. Verespei, Vista, all of CA (US)

(73) Assignee: DJ Orthopedics, LLC, Vista, CA (US)

( * ) Notice: Subject to any disclaimer, the term of this patent is extended or adjusted under 35 U.S.C. 154(b) by 0 days.

(21) Appl. No.: 09/589,894

(22) Filed: Jun. 7, 2000

Related U.S. Application Data

(62) Division of application No. 09/326,384, filed on Jun. 4, 1999.

(51) Int. Cl.[7] .................................................. A61F 5/00
(52) U.S. Cl. ................................... 602/26; 602/5; 602/16
(58) Field of Search .............................. 602/5, 16, 20, 602/21, 26, 27

(56) References Cited

U.S. PATENT DOCUMENTS

| 3,786,804 | * | 1/1974 | Lewis ...................................... 128/80 |
| 4,064,874 | * | 12/1977 | Valin ....................................... 128/80 |
| 4,697,583 | * | 10/1987 | Mason et al. .......................... 128/80 |
| 4,941,462 | * | 7/1990 | Lindberg ................................ 128/80 |
| 5,669,873 | * | 9/1997 | Towsley ................................. 602/26 |
| 5,749,840 | * | 5/1998 | Mitchell et al. ......................... 602/5 |
| 5,865,777 | * | 2/1999 | Detty ..................................... 602/26 |

FOREIGN PATENT DOCUMENTS

| 0174216 | * | 3/1986 | (EP) . |
| 0 174 216 | | 3/1986 | (EP) . |
| 0290409 | * | 4/1988 | (EP) . |
| 0 290 409 | | 4/1988 | (EP) . |
| 93/20782 | * | 10/1993 | (WO) . |
| WO 93/20782 | | 10/1993 | (WO) . |
| 98/14144 | * | 4/1998 | (WO) . |
| WO 98/14144 | | 4/1998 | (WO) . |

* cited by examiner

*Primary Examiner*—Kim M. Lewis
(74) *Attorney, Agent, or Firm*—Knobbe, Martens, Olson & Bear, LLP (57) ABSTRACT

Braces for loading and/or unloading knees, elbows and other joints. Such braces feature a stiffener which may be substantially permanently configured in shape to cooperate with the brace in applying tension to locations on the limb proximal and distal to the joint being loaded and/or unloaded, which counteract forces applied by the stiffener to the joint. A bending tool which may be accompanied by use of a goniometer may be employed for proper configuration of the stiffener using the wearer's limb geometry as a reference. Such braces are particularly effective for treating conditions such as compartmental osteoarthritis.

4 Claims, 7 Drawing Sheets

DEVICE FOR CONFIGURING A JOINT BRACE

RELATED APPLICATIONS

The present application is a divisional of U.S. Patent Application Ser. No. 09/326,384 filed Jun. 4, 1999, the entire contents of which is hereby incorporated by reference.

The present invention relates to braces for applying forces to knees and other joints in a medial/lateral plane or as otherwise desired. Such braces employ stiffeners which may be preferably removed and configured to a desired shape for imparting a predetermined force on the joint when employed in the joint brace.

BACKGROUND OF THE INVENTION

Conventional approaches to compartmental osteoarthritis and other joint maladies have included placing a brace on the limb surrounding the joint. Such braces aim to impart force or leverage on the joint in order to relieve compressive forces within a portion of the joint, or to reduce the load on that portion. For instance, in knee compartmental osteoarthritis situations, braces have been employed which feature rigid bars situated on the leg opposite or adjacent to the affected compartment of the knee. The bars include medial/lateral hinges which allow portions of the bars to be pivoted or swiveled in the frontal (varus/valgus) plane with respect to one another and locked into a desired configuration. The brace so configured when installed on the knee then imparts leverage at least partially to unload the affected compartment, and the adjustable hinges allow the magnitude of the force to be controlled or varied. Such adjustable hinges may employ set screws or other adjustment structure. Often, however, the adjustment structure requires use of a special tool and virtually always introduces bulkiness accompanied, paradoxically, by structural compromise and complexity.

SUMMARY OF THE INVENTION

The present invention provides braces for loading and unloading joints which alleviate the need for medial/lateral structure configuration adjustment devices such as hinges. Braces according to the present invention include a stiffener. The stiffener is preferably removably attached to the brace so that it can be adjusted in configuration while apart from the brace. The configuration of the stiffener may be permanently or substantially permanently adjusted or deformed by bending. In one version of the invention, the bending may occur in a bending tool which may include a goniometer for measuring the degree of deformation of, and the consequent loading to be applied by, the stiffener.

The stiffener so placed in the bending tool and bent to a desired configuration is deformed in a manner that is permanent or at least substantially permanent in the range of temperatures and forces encountered by the average brace wearer. The stiffener so configured is attached to or inserted in the brace, which may be formed of elastic, non-elastic or partially elastic material. The brace when installed properly on a limb loads or unloads portions of the joint with a predetermined force, a proxy for whose magnitude may, but need not be, determined by measuring a patient's limb alignment with a goniometer and configuring the stiffener with a bias relative to the patient's limb alignment. The amount of bias then corresponds to the magnitude of that force.

The stiffeners may be formed of metal, in which case bending for permanent or substantially permanent deformation may occur at room temperature. Stiffeners may also be formed of desired plastics or composite materials in which case bending for permanent or substantially permanent deformation can occur while heated; when the stiffener returns from its temperature excursion to the normal range of temperatures encountered by brace wearers, the deformation imparted by the bending is permanent and/or semi-permanent. That is, application of loads to the stiffener while the brace is in use does not cause the shape of the stiffener to "creep" or relax back to its previous, preconfiguration shape, or to suffer substantial plastic deformation. The stiffener instead "springs back" to its deformed configuration when the loads are removed.

It is accordingly an object of the present invention to provide knee braces for medial/lateral loading and unloading of body joints which employ stiffeners whose configuration may be readily adjusted to control the degree of loading and/or unloading, but which are inexpensive and efficient to manufacture.

It is an additional object of the present invention to provide braces for loading and unloading body joints whose stiffeners may be configured in shape without the need for special hinges or configuration structure such as set screws.

It is an additional object of the present invention to provide braces for loading and unloading body joints which include stiffeners whose configuration may be adjusted to a desired shape using a measuring device which may be adjusted to conform to the geometry of the leg and then used to configure the stiffener to apply proper loading.

It is an additional object of the present invention to provide braces for loading and unloading body joints whose stiffeners may be configured in shape using a bending tool and accompanying goniometer to control conformance to limb geometry, and/or, if desired, the magnitude, recordability and repeatability of the configuration change and consequent loading/unloading on the body joint.

It is an additional object of the present invention to provide braces for loading and unloading body joints whose stiffeners may be manually configured simply by being bent to a desired and predetermined shape to control and impart loading and/or unloading to the body joint, but which do not relax back to their non-configured shape as a result of such loading and/or unloading.

It is an additional object of the present invention to provide braces for loading and unloading body joints and which may be easily and quickly adjusted by a clinician in a manner that requires only a single visit by the patient.

Other objects, features and advantages of the present invention will become apparent with respect to the remainder of this document.

BRIEF DESCRIPTION OF THE DRAWINGS

FIG. 1A is a front elevational view of a brace according to a second embodiment of the present invention.

FIG. 1B is a schematic front elevational view of a brace according to a third embodiment of the present invention.

DETAILED DESCRIPTION OF THE DRAWINGS

Figure 1:
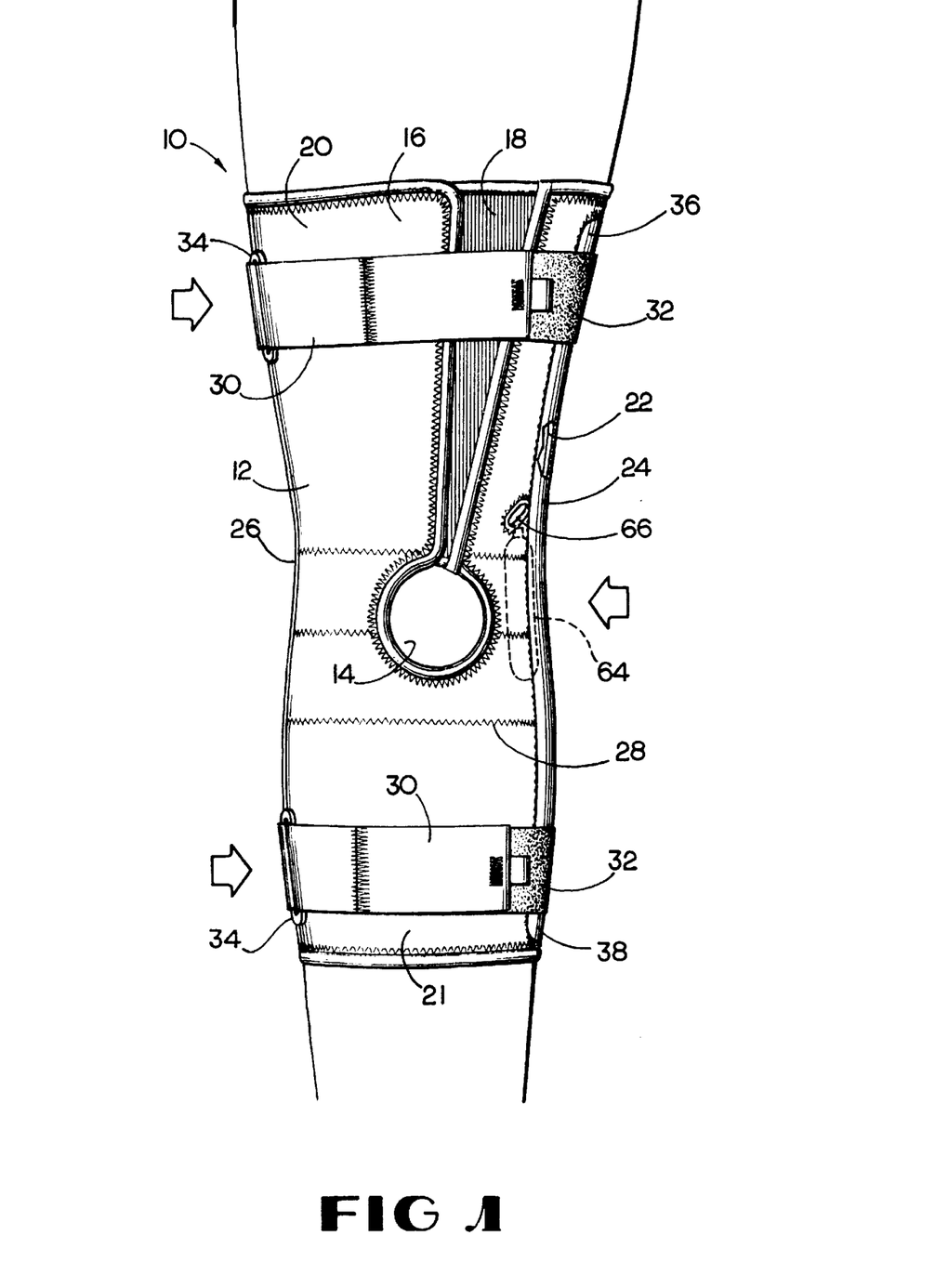
FIG. 1 is a front elevational view of a brace according to a first embodiment of the present invention.
Figure 2:
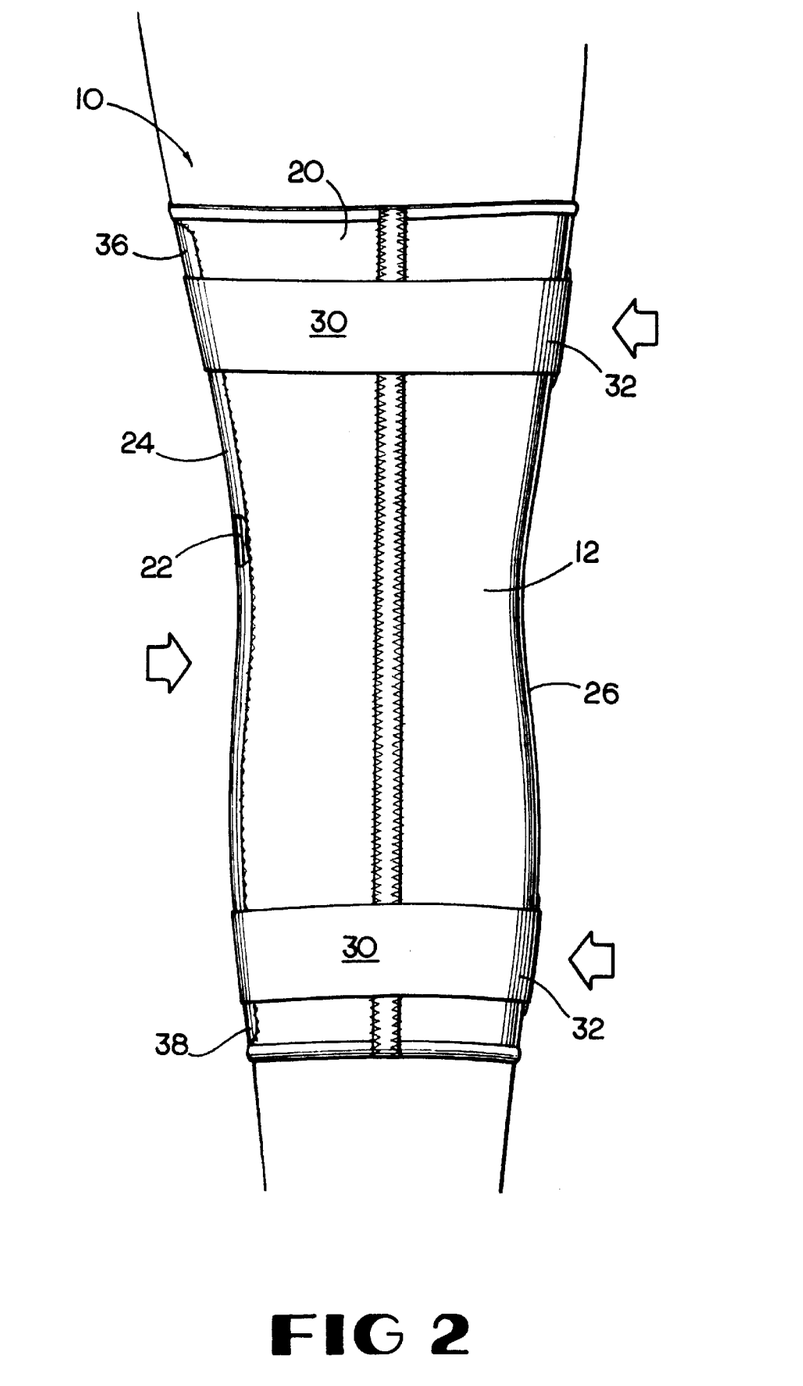
FIG. 2 is a rear view of the brace of FIG. 1.

FIGS. 1 and 2 show a first embodiment of a brace 10 according to the present invention. Brace 10 is shown applied on the left leg of a wearer. FIG. 1 is a front-on view of the left leg of the wearer, while FIG. 2 is a rear view of the left leg of the wearer with the brace 10 applied.

Brace 10 shown in FIGS. 1 and 2 is formed of a sleeve 12 in combination with a number of other components. Sleeve 12 may be formed of any desirable fabric such as fully-, non-, or partially-stretchable fabric which may or may not be breathable. Sleeve 12 may be fabricated using conventional stitching to conform to knees, elbows or other body joints as desired. Sleeve 12 in the embodiment shown in FIGS. 1 and 2 features a knee cap opening 14 in order to alleviate pressure directly on the patella and, if desired, for stabilization of the patella relative to other parts of the knee. In the embodiment shown in FIGS. 1 and 2, opening 14 initiates a discontinuity in sleeve 12 which allows adjustment dimensionally about the thigh. The discontinuity shown in FIGS. 1 and 2 is a flap 16. Flap 16 cooperates with a corresponding section 18 of sleeve 12 to allow flap 16 to be fastened removably to section 18 so that the upper or proximal portion 20 of sleeve 12 may be dimensioned to the body part (here, thigh) for a comfortable, secure fit. (Distal portion 21 of sleeve 12 could also contain a discontinuity if desired.) Flap 16 may be removably attached to section 18 using hook and loop fastener or any other desired fastening structure. Sleeve 12 need not contain any discontinuity such as flap 16/section 18, or knee cap opening 14. Flap 16 may be oriented at any angle or direction as desired; its leading edge may be inclined, as shown in FIG. 1, for example, or the opposite direction.

Sleeve 12 contains on one side (which may correspond to the lateral or medial side of the leg or other limb when the brace is worn) a stiffener 22 which may be removably enclosed in a stiffener sheath 24. Sheath 24 may be a fabric section sewn to sleeve 12, a pocket, or any other structure which attaches stiffener 22 to sleeve 12, whether removably or in a manner which fixes the position of stiffener 22 relative to sleeve 12. In the preferred embodiment, sheath 24 is a pocket structure formed by stitching material to sleeve 12; the pocket is generally configured in shape to conform to the shape of the stiffener 22. A slit 23 at one end of the sheath 24 allows the stiffener 22 to be inserted and removed. Stiffener 22 and portions of the sheath 24 may feature hook and loop patches in order to reduce the possibility that stiffener 22 would rotate relative to sheath 24 and sleeve 12.

The side of sleeve 12 opposite the side featuring the stiffener sheath 24 may include an anchor 26 such as a tube or additional thickness of material sewn or otherwise attached to the sleeve 12. Anchor 26 may help reduce or limit migration and bunching of sleeve 12. Such lines of stitching 28 and additional material are not required, but they may be employed as desired for additional stabilization, cushioning, fit and feel. Stiffener sheath 24 and anchor 26 may also serve as an anchor for distribution of forces from lines of stitching 28 or other portions of sleeve 12 or brace 10.

Brace 10 shown in FIG. 1 also includes at least two tensioning structures 30 for applying tension to portions of stiffener 22 relative to the body part distally and proximally of the joint circumscribed by the brace 10. In the embodiment shown in FIGS. 1, 2 and 3, tensioning structures 30 may be straps 32 which may be, but need not be, fastened to sleeve 12 and which may be tightened and fastened to themselves or portions of brace 10 in order to tension stiffener 22 portions relative to the limb being treated. In the embodiments shown in FIGS. 1, 2 and 3, tensioning structures 30 (straps 32) are attached to the sleeve 12 by stitching at loops 34, which may be plastic D rings or other devices. Loops 34 obviously need not be included. Straps 32 preferably circumscribe the leg of the wearer; one end with hook/loop fastener material extends through a loop 34 and fastens back onto itself for a 200% mechanical advantage using hook/loop material on another portion of the strap 32. Tensioning structures 30 may be any structure, whether or not attached to sleeve 12 or constituting portions of the sleeve 12, which tension portions of stiffener 22 against the body part to which the brace 10 is applied. Tensioning structures 30 may, for instance, as shown in FIG. 1A, be portions of sleeve 12 or structures within sleeve 12. Elastic or nonelastic members, members integral to or that are simply a part of sleeves 12 and any other structure appropriate to tension stiffener 22 portions against the leg or body part both distally and proximately of the joint can serve the function of tensioning structures 30 according to present invention, regardless of what particular structural niceties may be involved or which particular way they may apply such tension. The effect or result is to cause stiffener 22 to pull both distal and proximal portions of the limb toward stiffener 22 while pushing the joint circumscribed by the brace away from stiffener 22 thereby to impart relative force or leverage to the joint and thus reduce the load on the side of the joint opposite to the side in which stiffener 22 is located. (Such reduction in the loading on portions of a joint, whether partially or completely may sometimes be referred to as "unloading." Simultaneously with such unloading, complementary loading of other portions of the joint occurs. Accordingly, the application of force on part of or all of the joint by stiffener or brace or portions of them may be referred to as "unloading," "loading," "reducing the load" on the joint or portions of it.)

In the embodiment shown in FIG. 1, the stiffener 22 on the lateral side of the left knee reduces the load on the medial compartment of the knee for treatment of medial side compartmental osteoarthritis of the knee. Brace 10 may be manufactured for the left and right legs, respectively, and further manufactured for unloading of lateral or medial sides of the joint for each of those legs. Thus, for instance, two versions of left leg braces may be manufactured, one accommodating a stiffener 22 on its lateral side for treatment of the medial side of the knee, and one for accommodating a stiffener 22 on its medial side for unloading of the lateral side of the knee. Brace 10 may also be manufactured to feature a stiffener sheath 24 on each of its sides for treatment for medial or lateral side of the joint, and/or for left or right limb, in order to minimize inventory and manufacturing diversity requirements.

FIGS. 1 and 1A also show (in relief) an inflatable cushion or condyle 64 interposed between the stiffener 22 and the joint being treated. The condyle 64, which may be a conventional inflatable condyle, may be inflated using a conventional inflation device 68 such as shown in FIG. 1A, through slot 66 in sleeve 22. Inflation/deflation modes of hand pump device 68 may be mediated through valve control and valve 70. Other sorts of condyles, including non inflatable ones, and other sorts of inflation devices may also be used.

Figure 3:
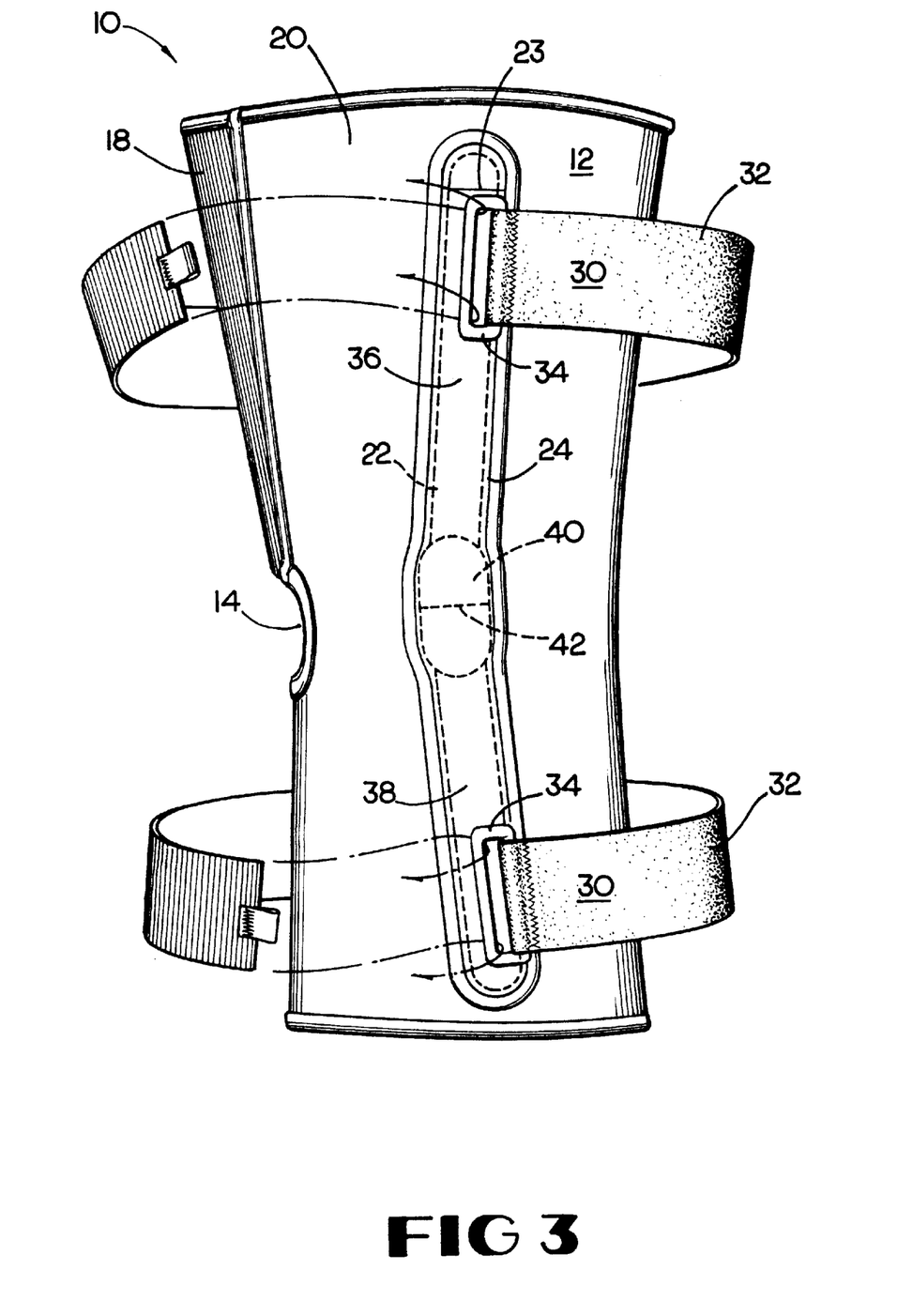
FIG. 3 is a left side elevational view of a second embodiment of a brace according to a third embodiment of the present invention, showing a stiffener in outline.

FIG. 2 shows a rear view of the brace shown in FIG. 1, and FIG. 3 shows a side view of a brace whose straps 32 are attached on the side of the brace 10 on which stiffener 22 and stiffener sheath 24 are located.

FIG. 1B shows in a schematic manner another embodiment of a brace 10 according to the present invention where the stiffener 22 is to be located on the same side of the knee as the compartment to be unloaded. Here, proximal portion 36 and distal portion 38 of the stiffener 22 are curved inward toward the limb, rather than outward from the limb as in FIG. 1. The effect or result is to cause stiffener 22 to pull the joint circumscribed by the tensioning structure 80 towards the stiffener 22 while pushing both distal and proximal portions of the limb away from the stiffener.

FIG. 3 shows a stiffener 22 in relief enclosed in a stiffener sheath 24. Stiffener 22 may include a proximal portion 36, a distal portion 38 and a connector 40 which structurally connects proximal portion 36 and distal portion 38 but allows them to rotate or otherwise move relative to each other to accommodate movement of the body joint circumscribed by brace 10. In the embodiment shown in FIG. 3, connector 40 is a bicentric hinge of the sort disclosed in U.S. Pat. No. 4,697,583 to Mason, et. al., which is incorporated herein by this reference. Gears in such hinge permit only controlled rotation of proximal portion 36 relative to the distal portion 38, so that horizontal axis 42 of connector 40 bisects the angle formed by proximal portion 36 and distal portion 38. Connector 40 may be a monocentric hinge, a non geared bicentric hinge, or any other linkage or structure which may be desired to accommodate movement of the body joint; it may, in cases where no movement is desired such as where the stiffener 22 acts as a splint, simply be part of the structure of the stiffener 22. Many such structures are conventional; for example, connector 40 may be formed of portions of proximal portion 36 and distal portion 38, such as versions in which a combination of slots in such members cooperate with pins to allow movement of the portions relative to each other.

Figure 4:
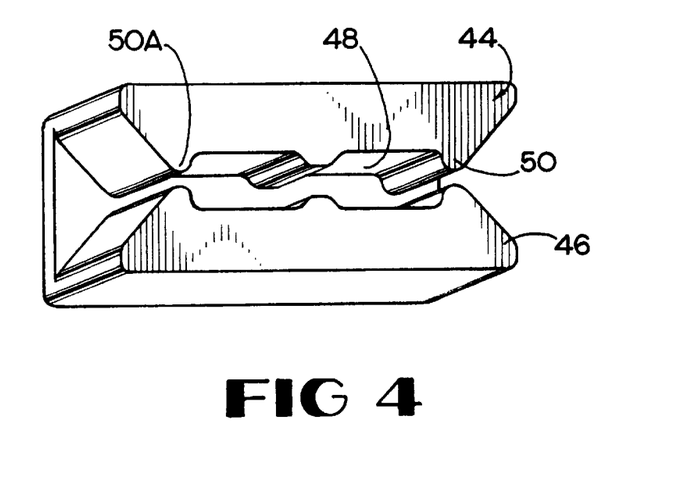
FIG. 4 is a perspective view of a bending tool according to the present invention for controllable configuration of the stiffeners of the braces of FIGS. 1–3.
Figure 4A:
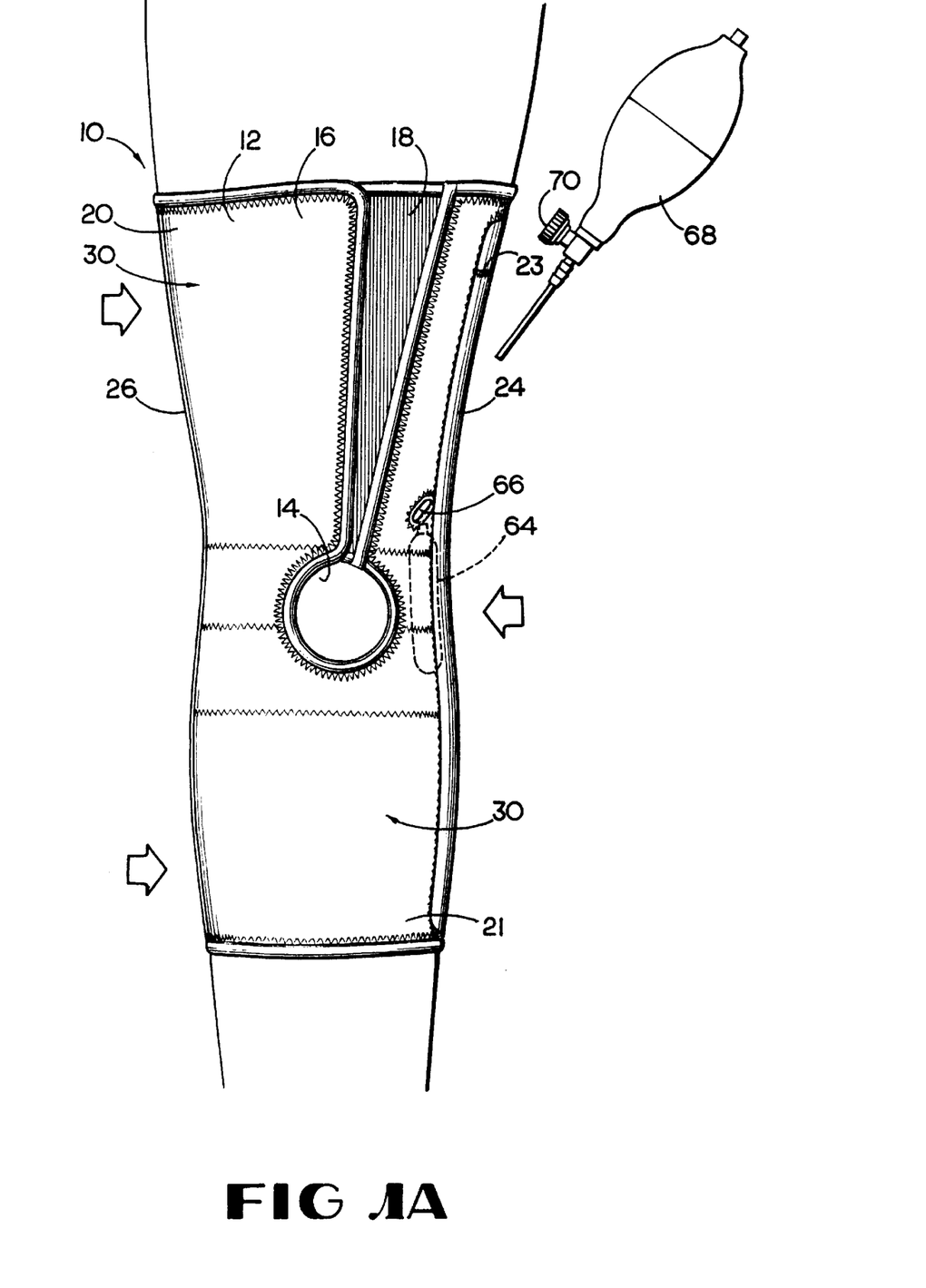
Figure 4B:
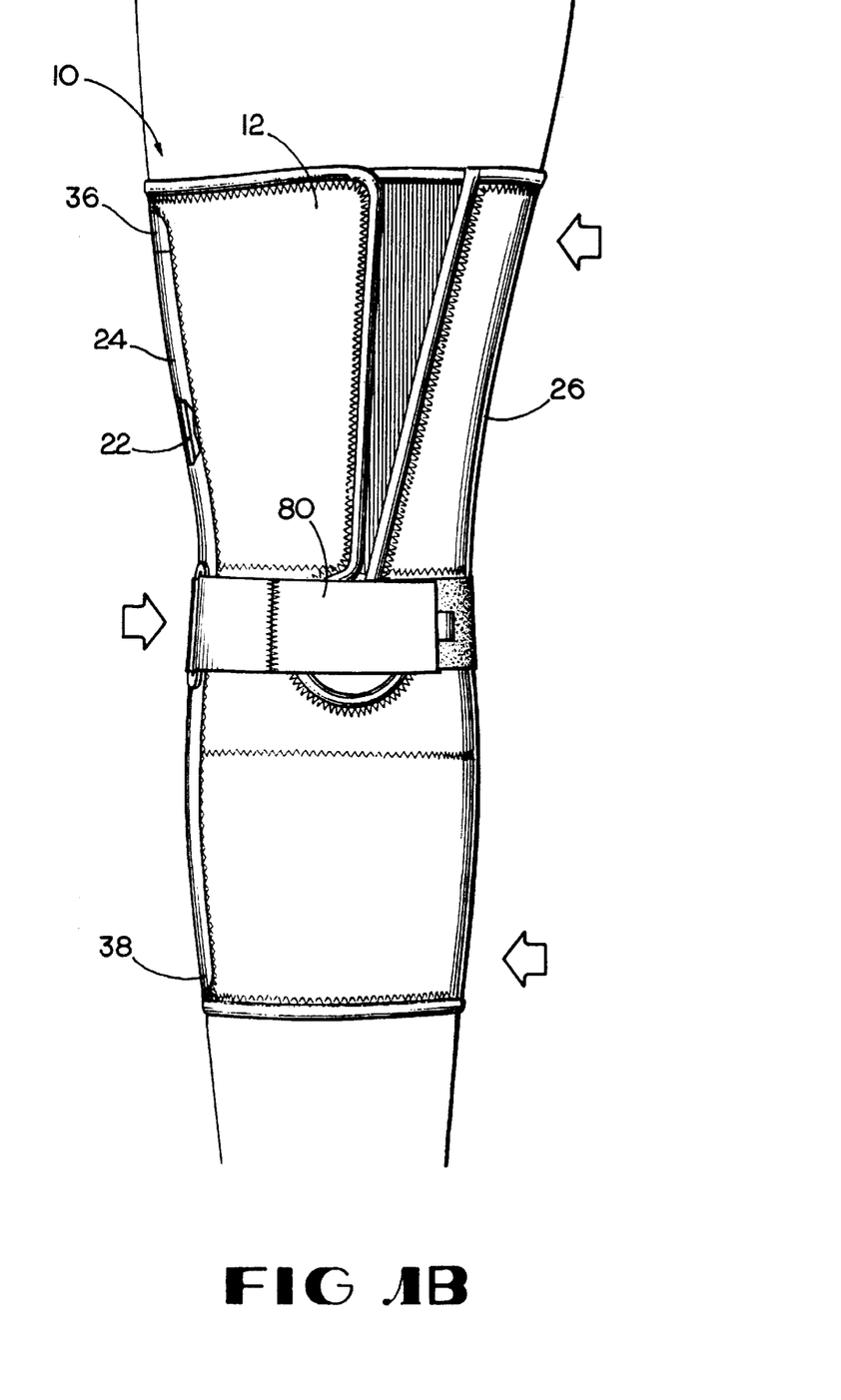
Figure 5:
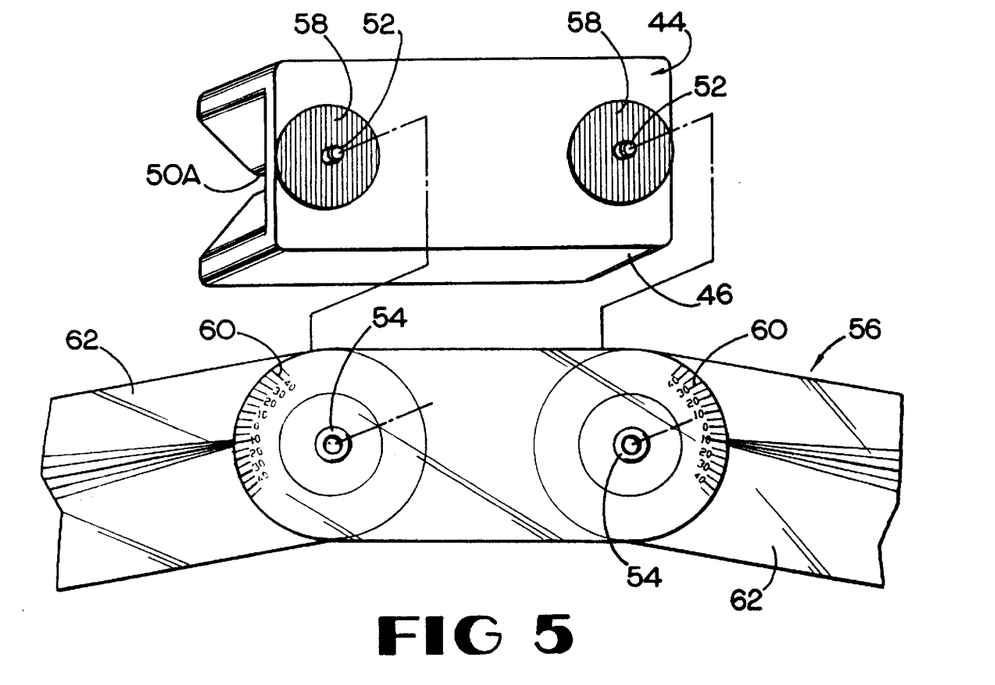
FIG. 5 is a rear perspective view of the bending tool of FIG. 4 in combination with a goniometer according to a preferred embodiment of the present invention.
Figure 6:
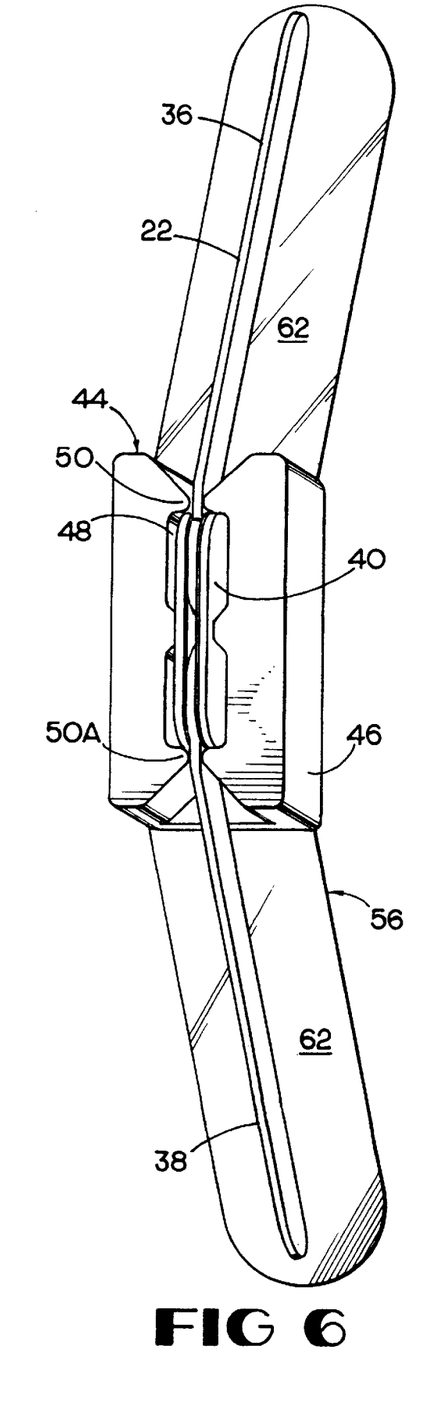
FIG. 6 is a perspective view of a brace stiffener according to a preferred embodiment of the present invention inserted into a bending tool with accompanying goniometer for controllable configuration and consequent body joint loading and unloading when the stiffener is installed in the brace and the brace properly applied; here, the stiffener is configured neutrally before being configured to load the knee as desired when installed in the brace of FIG. 1.

FIGS. 4–6 show a bending tool 44 for configuring stiffener 22 to apply proper loading and unloading to a joint circumscribed by brace 10. Device 44, whatever form it may take, seeks the result of allowing substantially permanent deformation of portions of stiffener 22 into a configuration which, when the stiffener 22 is used in combination with the structures on brace 10, allows the joint circumscribed by brace 10 to receive loading and/or unloading forces of a magnitude and in a direction as desired for effective treatment or therapy. The term "substantially permanent deformation" means that when the stiffener 22 as properly configured is used in combination with brace 10 to load and/or unload the joint, the bending of the stiffener 22 in its spring like fashion to load and/or unload the joint will not cause the configuration of the stiffener 22 (at normal temperatures encountered by the wearer) to creep or relax substantially to another shape such as, for instance, the shape it had before being deformed in device 44.

Stiffener 22 may be formed, for instance, of metal, or it may be formed of plastics or composite material. Metal stiffeners preferably feature a structure and modulus of elasticity which allow manual substantially permanent deformation. Manual bending is an acceptable form of substantially permanent deformation in such cases. For instance, and in general, causing proximal and distal portions 36 and 38 respectively to be oriented more outwardly from the limb can be expected to cause stiffener 22 to impart greater unloading to the medial compartment of the knee shown in FIG. 1. By contrast, causing such portions to be oriented more inwardly toward the limb can be expected to cause stiffener 22 to impart greater unloading to the medial comparatment of the knee shown in FIG. 1B.

Stiffener 22 formed of plastics or composite may be of a sort which can be heated prior to or during the bending operation, as by use of a hair dryer, hot liquid or other suitable application of heat. After configuration and deformation, upon return of temperature to that normally encountered by the wearer of braces such as these, the modulus of elasticity of such stiffener 22 increases to a point where the stiffener 22 becomes spring-like rather than pliable or malleable so that stiffener 22 is thus able to impart loading and/or unloading to the joint circumscribed by brace 10.

Device 44 shown in FIG. 4 is one form of a device for substantially permanent deformation of the sort of stiffener 22 shown in FIG. 3 which features a bicentric hinge. Device 44, which may be formed of metal, plastic or any other desired material, features a body 46 with a cavity 48 adapted to receive the connector 40 and portions of proximal portion 36 and distal portion 38 of stiffener 22. Cavity 48 walls define two fulcra 50, 50A against and about which proximal portion 36 and distal portion 38 of stiffener 22 may be controllably bent or deformed. FIG. 6 shows a stiffener 22 in combination with device 44 for such substantially permanent deformation.

FIGS. 5 and 6 show use of a goniometer for measuring the degree of bending or deformation of each of proximal portion 36 and distal portion 38 of stiffener 22. Pins 52 on device body 46 receive grommets into the goniometer 56. Goniometer 56 may be permanently or removably attached to body 46 using hook/loop fastener 58 on goniometer 56 and device 44. Any other desired fastener may be used, or no fastener at all.

Device 44 may assume any shape or configuration expedient for the result of controllably substantially permanently deforming portions of stiffener. Alternatively, device 44 need not be used at all if not desired. A wearer or medical professional may simply bend or deform the stiffener 22 at any point along its length using whatever implements are deemed appropriate in order to create a shape and configuration that is substantially permanent and that properly loads and/or unloads the joint circumscribed by brace 10.

According to the embodiments shown in the Figures, the stiffener 22 may be configured by substantially permanently deforming it in device 44 or as otherwise desired in order to apply proper loading/unloading to the joint being treated. Indicia 60 and 61 on the goniometer 56 may be employed for this purpose. Indicia 60 may, but need not, appear on the central portion of the goniometer 56. Indicia 61 appear on arms 62. In practice, the clinician or qualified other person aligns arms 62 of goniometer 56 with the calf and thigh of the wearer's leg to be treated with brace 10 shown in FIG. 1; the position of the arms 62 may be noted using indicia 60. While the arms 62 of goniometer 56 are maintained in this position on the goniometer 56, the goniometer 56 may then be placed on device 44 for configuration of stiffener 22. As shown in FIG. 6, the proximal portion 36 and distal portion 38 of stiffener 22 may be manually bent in device 44 to align with a center index 61 on each arm 62; the stiffener has thus been configured to correspond in shape to the geometry of the limb of the wearer to be treated.

Figure 7:
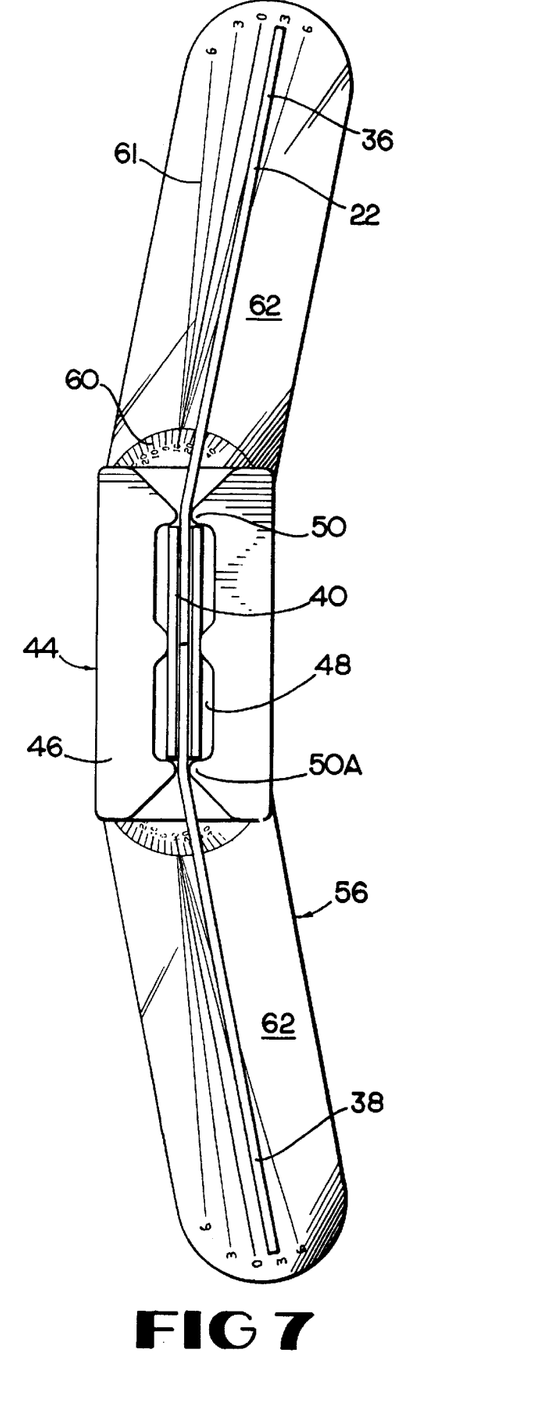
FIG. 7 is a top plan view of a brace stiffener according to a preferred embodiment of the present invention inserted into a bending tool with accompanying goniometer for controllable configuration and consequent body joint loading and unloading when the stiffener is installed in the brace and the brace properly applied; here, the stiffener is configured to apply relatively large force to the knee when installed in the brace of FIG. 1.

Stiffener 22 may then be configured, or configured continuously as part of the process stated in the previous sentence, in device 44 to orient proximal portion 36 and distal portion 38 as appropriate in order to load the joint properly. As shown in FIG. 7, indicia 61 on arms 62 of goniometer 56 may be used for this purpose. Orientation of portions 36 and 38 parallel to the zero degree indicia 61 results in neutral loading, since the stiffener is simply configured to the shape of the limb as reflected by the arms 62 being set relative to indicia 60 during the limb measuring steps mentioned above. Orientation of portions 36 and 38 substantially parallel to the six degree loading indicia 61 results in relatively large forces applied to the knee, while orientation substantially parallel to the three degree loading indicia results in relatively lighter forces applied to the knee.

After configuration, the stiffener is attached to the brace 10. Tensioning structures 30 are properly tensioned and fastened to apply tension to proximal portion 20 and distal portion 21 of the limb while the central portions of the stiffener 22 apply compressive forces to the joint in order to unload the side of joint opposite the stiffener 22. In a brace with no straps, flap 16 may be adjusted as desired to assist in this purpose. If the stiffener 22 is permanently attached to brace 10, it is configured by remaining within brace 10. Patient comfort and clinician empirical inspection may be employed, among other techniques, which may or may not involve conventional measurement apparatus, to ensure that tensioning structures 30 and stiffener 22 properly apply forces to load and/or unload the joint.

The foregoing is provided for purposes of explanation and disclosure of preferred embodiments of the present invention. Modifications, additions and/or deletions may be made to the structures where their components shown and described in this document without departing from the scope or spirit of the invention.

What is claimed is:

1. A device for configuring a joint brace, the brace comprising a sleeve adapted to circumscribe a proximal part of a wearer's limb, a distal part of the wearer's limb, and portions of the joint between the two parts of the wearer's limb, and a stiffener removably attached to one side of the brace, the stiffener comprising a proximal portion, a distal portion, and a connector allowing the proximal portion and distal portion to rotate relative to each other when the brace is installed on the wearer; the device comprising:

a. a body in which a portion of the stiffener may be placed, the body including a fulcrum about which a portion of the stiffener may be manually bent; and b. a goniometer attached to the body in the vicinity of the fulcrum for orienting the angles at which portions of the stiffener are bent relative to each other.

2. A device according to claim 1 in which the body features a cavity for receiving a bicentric connector, the cavity featuring two fulcra located in a position that corresponds to the centers of the bicentric connector, each fulcrum disposed in the cavity on opposite sides of a portion of the cavity that receives the bicentric connector, each fulcrum adapted to assist bending a portion of the stiffener.

3. A device according to claim 2 in which the goniometer is bicentric, the centers corresponding in location to the centers of the bicentric connector, the goniometer adapted to have each center positioned on the body in the vicinity of a fulcrum.

4. A device according to claim 3 in which the goniometer is removably attached to the body.

\* \* \* \* \*

UNITED STATES PATENT AND TRADEMARK OFFICE
CERTIFICATE OF CORRECTION

PATENT NO.     : 6,238,360 B1
DATED          : May 29, 2001
INVENTOR(S)    : Gildersleeve et al.

It is certified that error appears in the above-identified patent and that said Letters Patent is hereby corrected as shown below:

<u>Title page,</u>
Item [62], please delete "09/326,384, filed on Jun. 4, 1999" and replace with
-- 09/079,956, filed on May 15, 1998 --.

Signed and Sealed this

Twenty-first Day of October, 2003

JAMES E. ROGAN
*Director of the United States Patent and Trademark Office*